(12) United States Patent
Asir et al.

(10) Patent No.: US 8,404,460 B2
(45) Date of Patent: Mar. 26, 2013

(54) **METHOD FOR DETECTING AND/OR IDENTIFYING *CLOSTRIDIUM DIFFICILE***

(75) Inventors: Kerry Asir, Dudley (GB); Marie-Pierre Bourguignon, Vertrieux (FR); Diane Halimi, Saint-Maurice-de-Beynost (FR); John Perry, Newcastle (GB); Sylvain Orenga, Neuville sur Ain (FR)

(73) Assignee: Biomerieux, Marcy l'Etoile (FR)

( * ) Notice: Subject to any disclaimer, the term of this patent is extended or adjusted under 35 U.S.C. 154(b) by 184 days.

(21) Appl. No.: 12/810,396

(22) PCT Filed: Jan. 20, 2009

(86) PCT No.: PCT/FR2009/050072
§ 371 (c)(1),
(2), (4) Date: Jun. 24, 2010

(87) PCT Pub. No.: WO2009/092982
PCT Pub. Date: Jul. 30, 2009

(65) Prior Publication Data
US 2010/0279330 A1    Nov. 4, 2010

(30) Foreign Application Priority Data
Jan. 21, 2008  (FR) .................................. 08 50354

(51) Int. Cl.
*C12Q 1/34*  (2006.01)
(52) U.S. Cl. .......................................... 435/18
(58) Field of Classification Search .................. None
See application file for complete search history.

(56) References Cited

U.S. PATENT DOCUMENTS

| | | | |
|---|---|---|---|
| 5,635,367 A | 6/1997 | Lund | |
| 6,287,798 B1 | 9/2001 | James et al. | |
| 6,340,573 B1 * | 1/2002 | Armstrong et al. | 435/18 |
| 2007/0004021 A1 | 1/2007 | Restaino | |

FOREIGN PATENT DOCUMENTS

| WO | WO 97/41138 A2 | 11/1997 |
|---|---|---|
| WO | WO 01/42490 A2 | 6/2001 |

OTHER PUBLICATIONS

Fontan et al. Microbiol. Immunol. (1995) 39(4), 235-235.*
"System for the identification of anaerobes," REF 20 300 api 20 A, 2006.
"Identification system for anaerobes," REF REF 32 300 rapid ID 32 A, 2006.
Reyes et al., "Performance of TechLab C. Diff Quick Chek™ and TechLab C. Difficile TOX A/B II™ for the detection of *Clostridium difficile* in stool samples," *Diagnostic Microbiology and Infectious Disease*, 2007, vol. 59, pp. 33-37.
Russmann et al., "Evaluation of three rapid assays for detection of *Clostridium difficile* toxin A and toxin B in stool specimens," *Eur. J. Clin. Microbiol. Infect. Dis.*, 2007, vol. 26, pp. 115-119.
George et al., "Selective and Differential Medium for Isolation of *Clostridium difficile*," *Journal of Clinical Microbiology*, 1979, vol. 9, No. 2, pp. 214-219.
Written Opinion of the International Searching Authority in International Application No. PCT/FR2009/050072; dated Sep. 14, 2010.
International Search Report in International Application No. PCT/FR2009/050072; dated Sep. 24, 2009 (with English-language translation).

* cited by examiner

*Primary Examiner* — Nashaat Nashed
(74) *Attorney, Agent, or Firm* — Oliff & Berridge, PLC

(57) ABSTRACT

The invention relates to a method for detecting and/or identifying *Clostridium difficile*, characterized in that it comprises the following steps:
a) providing a reaction medium comprising at least one beta-glucosidase substrate capable of identifying *C. difficile*,
b) inoculating the medium with a biological sample to be tested,
c) allowing for incubation, and
d) detecting the hydrolysis of the beta-glucosidase substrate, indicative of the presence of *Clostridium difficile*.

The invention also relates to a reaction medium for the detection and/or the identification of *Clostridium difficile*, that comprises at least one beta-glucosidase substrate capable of identifying *C. difficile*.

11 Claims, No Drawings

METHOD FOR DETECTING AND/OR IDENTIFYING *CLOSTRIDIUM DIFFICILE*

The present invention relates to a reaction medium specific for *Clostridium difficile*. It also relates to a method for detecting and/or identifying *Clostridium difficile* which uses such a medium.

*Clostridium difficile* is a commensal microorganism of the intestinal flora. *Clostridium difficile* spores are found in the soil and in hospitals, the active form being found only in the intestines. Under the microscope, after Gram staining, they are elongated bacilli with a slightly bulging end. Since *Clostridium difficile* is resistant to most antibiotics, it can therefore develop considerably in the event of disruption of the intestinal flora by treatment with antibiotics. It then secretes two toxins, A and B, an enterotoxin and a cytotoxin, responsible for pseudomembranous colitis or for post-antibiotic diarrhea. As a result, *Clostridium difficile* is currently acknowledged to be a major enteropathogen, predominantly involved in nosocomial diarrhea in adults.

The diagnosis is based on various techniques, such as detection of the toxin activity (cytotoxicity activity, CTA). However, this technique has drawbacks, such as, in particular, the amount of time required to implement it, and the need for the expertise of technicians in order to read the results.

The diagnosis can also be carried out by immunology, by means of an ELISA assay. It is, however, recommended to combine the immunological techniques used for detecting the toxins with bacterial culture in order to isolate the strains of *Clostridium difficile*. This culturing step can be carried out on a *Clostridium difficile* agar sold by bioMerieux, the *Clostridium difficile* colonies then being identified by chemical methods, for example by using strips such as the API 20 A strips or the RAPID ID 32 A strips. However, the identification using strips requires a pure culture, of the bacterium to be identified, on a suitable growth medium in order to obtain sufficient biomass (3 to 4 Mc Farland), which at best takes 48 h (culture for isolation, for 24 to 72 hours, starting from the sample giving only the presumptive detection, plus culturing for 24 to 72 hours so as to generate sufficient biomass). The strip is then read after incubation for 4 h for the RAPID ID 32 A strip and 24 to 48 h for the API 20 A strip.

Finally, the diagnosis can be carried out by molecular biology techniques. These techniques are not, however, routinely used at this time.

Surprisingly, the inventors have demonstrated that the use of one or more beta-glucosidase enzyme substrate(s) allows easy and rapid identification of *Clostridium difficile*. This result is completely unexpected since the beta-glucosidase test of the rapid ID 32 A RAPID ID 32 A strip is negative for this species. The medium according to the invention allows detection and definitive identification from the sample from 24 h onward.

Before presenting the invention, the following definitions are given so as to make it possible to understand the invention more clearly. They are in no way limiting.

The term reaction medium is intended to mean a medium comprising all the elements necessary for the expression of a metabolism and/or for the growth of microorganisms. The reaction medium may be solid, semi-solid or liquid. The term "solid medium" is intended to mean, for example, a gelled medium. Agar is the conventional gelling agent in microbiology for culturing microorganisms, but it is possible to use gelatin, agarose or other natural or artificial gelling agents. A certain number of preparations are commercially available, such as, for example, Columbia agar, Trypticase-soy agar, MacConkey agar, Sabouraud agar or, more generally, those described in the Handbook of Microbiological Media (CRC Press). The reaction medium according to the invention should allow the growth of *C. difficile*.

The reaction medium may comprise one or more elements in combination, such as amino acids, peptones, carbohydrates, nucleotides, minerals, vitamins, etc. The medium may also comprise a colorant. By way of indication, as a colorant, mention may be made of Evans blue, neutral red, sheep blood, horse blood, an opacifier such as titanium oxide, nitroaniline, malachite green, brilliant green, one or more metabolic indicators, one or more metabolic regulators, etc.

The reaction medium may be a revealing medium, or a culture and revealing medium. In the first case, the microorganisms are cultured before inoculation and, in the second case, the detection and/or identification medium also constitutes the culture medium.

Those skilled in the art may also use a biplate, making it possible to readily compare two media, comprising various substrates or various selective mixtures, onto which the same biological sample will have been deposited.

The reaction medium may comprise one or more β-glucosidase inducers.

The term beta-glucosidase inducer is intended to mean a compound which induces an increase in the expression of the metabolic activity targeted; all experimental conditions being otherwise equal, the metabolic activity is higher when the inducer is at a suitable concentration than when it is absent or at an unsuitable concentration.

Mention may in particular be made of a carbohydrate constituted of a radical linked in the β-position to glucose or a carbohydrate with a β-glucoside sub-unit, in particular cellobiose, cellulose, starch, cellobiose, trehalose or methyl-β-glucoside. Without being limiting, a concentration of between 100 ng/l and 10 g/l, preferably between 1.0 mg/l and 3 g/l, is particularly suitable for the present invention.

The reaction medium may comprise one or more growth activators for *C. difficile* strains. The term growth activator is intended to mean a compound or a group of compounds which stimulates the growth of microorganisms. Mention may in particular be made of blood, serum and egg yolk.

Without being limiting, a concentration of between 0.1% and 10% is particularly suitable for the present invention.

The reaction medium may comprise one or more reducing agents.

The term reducing agent is intended to mean a compound or a group of compounds which facilitates the growth of anaerobic microorganisms by neutralizing the dissolved $O_2$ present in the medium. Mention may in particular be made of cysteine, pyruvate, OXYRASE, sodium sulfite, dithionite, histidine and ferrous sulfide.

Without being limiting, a concentration of between 0.05 and 50 g/l, preferably between 0.1 and 2 g/l, is particularly suitable for the present invention.

The reaction medium may comprise one or more *C. difficile* spore germination inducers. The term spore germination inducer is intended to mean a compound or a group of compounds which promotes the change from the spore state to the vegetative state of *C. difficile*. Mention may in particular be made of sodium taurocholate.

Without being limiting, a concentration of between 0.1 and 10 g/l, preferably between 1 and 5 g/l, is particularly suitable for the present invention.

The reaction medium may comprise one or more selective agents.

The term selective agent is intended to mean any compound capable of preventing or slowing down the growth of a microorganism. Without being limiting, a concentration of between 5 mg/l and 5 g/l is particularly suitable for the present invention.

As selective agent, mention may be made of an antibiotic such as D-cycloserine, cephalosporins, such as cefoxitin or cefotaxime, colistin, polymyxin, fosfomycin, tobramycin, gentamicin, aztreonam, trimethoprim, quinolones such as nalidixic acid, an antifungal such as, in particular, amphotericin B, fluconazole or itraconazole.

The term "antibiotic" is intended to mean any compound capable of preventing or slowing down the growth of a bacterium. They belong in particular to the cephalosporin, aminoglycoside, polypeptide, sulfamide and quinolone groups. By way of indication, mention may in particular be made of the antibiotics cefotaxime, ceftazidime, cefoxitin, ceftriaxone, cefpodoxime, aztreonam, trimethoprim, tobramycin, moxalactam, fosfomycin, D-cylcoserine, polymyxin and colistin.

The term "antifungal" is intended to mean any compound capable of preventing or slowing down the growth of a yeast or of a mold. By way of indication, mention may in particular be made of amphotericin B, fluconazole, itraconazole, voriconazole and cycloheximide.

The reaction medium may comprise a second enzyme substrate, such as, in particular, an osidase substrate, an esterase substrate, a peptidase substrate, etc. It may be a substrate which targets an enzyme expressed by *Clostridium difficile*, such as proline aminopeptidase, or an enzyme which is not expressed by *C. difficile*, such as β-ribosidase. The term substrate is intended to mean a molecule that can be hydrolyzed by an enzyme, such as beta-glucosidase, so as to give a product allowing the direct or indirect detection of a microorganism. This substrate comprises in particular a first part specific for the enzyme activity to be revealed and a second part which acts as a label, hereinafter referred to as label part. This label part may be chromogenic, fluorogenic, luminescent, etc.

The expression beta-glucosidase substrate capable of identifying *C. difficile* is intended to mean a substrate which, under suitable growth conditions, induces the coloration of *C. difficile*. Such substrates can in particular be selected by means of the test described in example 1.

Said expression is in particular intended to mean 2-hydroxyphenyl-β-glucoside (catechol-β-glucoside); magenta-β-glucoside (5-bromo-6-chloro-3-indoxyl-β-glucoside); DHF-β-glucoside (dihydroxyflavone-β-glucoside); esculin (esculetin-β-glucoside); CHE-β-glucoside (3,4-cyclohexenoesculetin-β-glucoside); 8-hydroxyquinoline-β-glucoside; X-3-glucoside (5-bromo-4-chloro-3-indoxyl-β-glucoside); pink-β-glucoside (6-chloro-3-indoxyl-β-glucoside); 6-bromo-3-indoxyl-β-glucoside; blue-β-glucoside (5-bromo-3-indoxyl-β-glucoside); 6-fluoro-3-indoxyl-β-glucoside; alizarin-β-glucoside; (P)-nitrophenyl-β-glucoside; 4-methylumbelliferyl-β-glucoside, naphtholbenzein-β-glucoside, indoxyl-N-methyl-β-glucoside, 5-bromo-4-chloro-3-indoxyl-N-methyl-β-glucoside, naphthyl-β-glucoside; aminophenyl-β-glucoside; dichloroaminophenyl-β-glucoside.

Preferably, the beta-glucosidase substrate capable of identifying *C. difficile* is chosen from 2-hydroxyphenyl-β-glucoside (catechol-β-glucoside); magenta-β-glucoside (5-bromo-6-chloro-3-indoxyl-β-glucoside); dihydroxyflavone-β-glucoside; esculin (esculetin-β-glucoside); 3,4-cyclohexenoesculetin-β-glucoside and alizarin-β-glucoside.

Preferably, the concentration of beta-glucosidase substrate in the medium according to the invention is between 25 and 1000 mg/l, and preferably between 50 and 400 mg/l.

The reaction medium may comprise a second enzyme substrate or several enzyme substrates, preferably chosen from an osidase substrate, an esterase substrate or a peptidase substrate.

The osidase substrate is intended to mean in particular alpha-glucosidase, galactosidase, ribosidase, hexosaminidase, glucuronidase, xylosidase, fucosidase, cellobiosidase, arabinosidase and mannosidase substrates.

The term "riboside" is intended to mean ribofuranoside and/or ribopyranoside. The term "arabinoside" is intended to mean arabinofuranoside and/or arabinopyranoside. The term "fucoside" is intended to mean D-fucoside and/or L-fucoside. When it is not specified, it may either be the α-glycoside or the β-glycoside.

The following are in particular intended: 5-bromo-6-chloro-3-indoxyl-α-glucoside; dihydroxyflavone-α-glucoside; 3,4-cyclohexenoesculetin-α-glucoside; 8-hydroxyquinoline-α-glucoside; 5-bromo-4-chloro-3-indoxyl-α-glucoside; 6-chloro-3-indoxyl-α-glucoside; 5-bromo-3-indoxyl-α-glucoside; alizarin-α-glucoside; nitrophenyl-α-glucoside; 4-methylumbelliferyl-α-glucoside; naphtholbenzein-α-glucoside; indoxyl-N-methyl-α-glucoside; 5-bromo-4-chloro-3-indoxyl-N-methyl-α-glucoside; naphthyl-α-glucoside; aminophenyl-α-glucoside; dichloroaminophenyl-α-glucoside; 2-hydroxyphenyl-galactoside; 5-bromo-6-chloro-3-indoxyl-galactoside; dihydroxyflavone-galactoside; 3,4-cyclohexenoesculetin-galactoside; 8-hydroxyquinoline-galactoside; 5-bromo-4-chloro-3-indoxyl-galactoside; 4-chloro-3-indoxyl-galactoside; 6-chloro-3-indoxyl-galactoside; 6-bromo-3-indoxyl-galactoside; 5-bromo-3-indoxyl-galactoside; 6-fluoro-3-indoxyl-galactoside; alizarin-galactoside; nitrophenyl-galactoside; 4-methylumbelliferyl-galactoside; naphtholbenzein-galactoside; indoxyl-N-methyl-galactoside; 5-bromo-4-chloro-3-indoxyl-N-methyl-galactoside; naphthyl-galactoside; aminophenyl-galactoside; dichloroaminophenyl-galactoside; 2-hydroxyphenyl-riboside; 5-bromo-6-chloro-3-indoxyl-riboside; dihydroxyflavone-riboside; 5-bromo-4-chloro-3-indoxyl-riboside; 6-chloro-3-indoxyl-riboside; 5-bromo-3-indoxyl-riboside; 6-fluoro-3-indoxyl-riboside; alizarin-riboside; nitrophenyl-riboside; 4-methylumbelliferyl-riboside; naphthyl-riboside; aminophenyl-riboside; dichloroaminophenyl-riboside; 2-hydroxyphenyl-N-acetyl-glucosaminide; 5-bromo-6-chloro-3-indoxyl-N-acetyl-glucosaminide; dihydroxyflavone-N-acetyl-glucosaminide; 3,4-cyclohexenoesculetin-N-acetyl-glucosaminide; 5-bromo-4-chloro-3-indoxyl-N-acetyl-glucosaminide; 6-chloro-3-indoxyl-N-acetyl-glucosaminide; 6-bromo-3-indoxyl-N-acetyl-glucosaminide; 5-bromo-3-indoxyl-N-acetyl-glucosaminide; 6-fluoro-3-indoxyl-N-acetyl-glucosaminide; alizarin-N-acetyl-glucosaminide; nitrophenyl-N-acetyl-glucosaminide; 4-methylumbelliferyl-N-acetyl-glucosaminide; 5-bromo-4-chloro-3-indoxyl-N-methyl-N-acetyl-glucosaminide; naphthyl-N-acetyl-glucosaminide; aminophenyl-N-acetyl-glucosaminide; dichloroaminophenyl-N-acetyl-glucosaminide; 5-bromo-6-chloro-3-indoxyl-glucuronide; dihydroxyflavone-glucuronide; 3,4-cyclohexenoesculetin-glucuronide; 8-hydroxyquinoline-glucuronide; 5-bromo-4-chloro-3-indoxyl-glucuronide; 6-chloro-3-indoxyl-glucuronide; 6-bromo-3-indoxyl-glucuronide; 5-bromo-3-indoxyl-glucuronide; 6-fluoro-3-indoxyl-glucuronide; alizarin-glucuronide; nitrophenyl-glucuronide; 4-methylumbelliferyl-glucuronide; naphtholbenzein-glucuronide; indoxyl-N-methyl-glucuronide; 5-bromo-4-chloro-3-indoxyl-N-methyl-glucuronide; naphthyl-glucuronide; aminophenyl-glucuronide; dichloroaminophenyl-glucuronide; 5-bromo-6-chloro-3-indoxyl-xyloside; dihydroxyflavone-xyloside; 5-bromo-4-chloro-3-indoxyl-xyloside; 6-chloro-3-indoxyl-xyloside; 5-bronco-3-indoxyl-xyloside; alizarin-xyloside; nitrophenyl-xyloside; 4-methylumbelliferyl-xyloside; naphthyl-xyloside; aminophenyl-xyloside; dichloroaminophenyl-xyloside; 5-bromo-6-chloro-3-indoxyl-fucoside; dihydroxyflavone-fucoside; 3,4-cyclohexenoesculetin-fucoside; 5-bromo-4-chloro-3-indoxyl-fucoside; 6-chloro-3-indoxyl-fucoside; 5-bromo-3-indoxyl-fucoside; alizarin-fucoside; nitrophenyl-fucoside; 4-methylumbelliferyl-fucoside; naphthyl-fucoside; aminophenyl-fucoside; dichloroaminophenyl-fucoside; 2-hydroxyphenyl-cellobioside; 5-bromo-6-chloro-3-indoxyl-cellobioside; dihydroxyflavone-cellobioside; 3,4-cyclohexenoesculetin-cellobioside; 8-hydroxyquinoline-cellobioside; 5-bromo-4-chloro-3-indoxyl-cellobioside;

6-chloro-3-indoxyl-cellobioside; 6-bromo-3-indoxyl-cellobioside; 5-bromo-3-indoxyl-cellobioside; 6-fluoro-3-indoxyl-cellobioside; alizarin-cellobioside; nitrophenyl-cellobioside; 4-methylumbelliferyl-cellobioside; naphtholbenzein-cellobioside; indoxyl-N-methyl-cellobioside; 5-bromo-4-chloro-3-indoxyl-N-methyl-cellobioside; naphthyl-cellobioside; aminophenyl-cellobioside; dichloroaminophenyl-cellobioside; 5-bromo-6-chloro-3-indoxyl-arabinoside; dihydroxyflavone-arabinoside; 5-bromo-4-chloro-3-indoxyl-arabinoside; 6-chloro-3-indoxyl-arabinoside; 5-bromo-3-indoxyl-arabinoside; alizarin-arabinoside; nitrophenyl-arabinoside; 4-methylumbelliferyl-arabinoside; 5-bromo-4-chloro-3-indoxyl-N-methyl-arabinoside; naphthyl-arabinoside; aminophenyl-arabinoside; dichloroaminophenyl-arabinoside; 5-bromo-6-chloro-3-indoxyl-mannoside; dihydroxyflavone-mannoside; 3,4-cyclohexenoesculetin-mannoside; 5-bromo-4-chloro-3-indoxyl-mannoside; 4-chloro-3-indoxyl-mannoside; 6-chloro-3-indoxyl-mannoside; 6-bromo-3-indoxyl-mannoside; 5-bromo-3-indoxyl-mannoside; alizarin-mannoside; nitrophenyl-mannoside; 4-methylumbelliferyl-mannoside; indoxyl-N-methyl-mannoside; 5-bromo-4-chloro-3-indoxyl-N-methyl-mannoside; naphthyl-mannoside; aminophenyl-mannoside; dichloroaminophenyl-mannoside. Without being limiting, a concentration of between 25 and 1000 mg/l is particularly suitable for the present invention.

Preferably, the osidase substrate is chosen from alpha-galactosidase, beta-galactosidase, hexosaminidase and cellobiosidase substrates, and in particular from: 5-bromo-4-chloro-3-indoxyl-galactoside; 5-bromo-6-chloro-3-indoxyl-N-acetyl-glucosaminide; 3,4-cyclohexenoesculetin-cellobioside; 5-bromo-4-chloro-3-indoxyl-cellobioside.

The term esterase substrate is intended to mean in particular 5-bromo-6-chloro-3-indoxyl-octanoate; dihydroxyflavone-octanoate; 5-bromo-4-chloro-3-indoxyl-octanoate; 6-chloro-3-indoxyl-octanoate; 6-bromo-3-indoxyl-octanoate; 5-bromo-3-indoxyl-octanoate; 6-fluoro-3-indoxyl-octanoate; alizarin-octanoate; nitrophenyl-octanoate; 4-methylumbelliferyl-octanoate; naphthyl-octanoate; aminophenyl-octanoate; dichloroaminophenyl-octanoate; 5-bromo-6-chloro-3-indoxyl-butyrate; 5-bromo-4-chloro-3-indoxyl-butyrate; 6-chloro-3-indoxyl-butyrate; 6-bromo-3-indoxyl-butyrate; 5-bromo-3-indoxyl-butyrate; alizarin-butyrate; nitrophenyl-butyrate; 4-methylumbelliferyl-butyrate; naphthyl-butyrate; aminophenyl-butyrate; dichloroaminophenyl-butyrate; 5-bromo-6-chloro-3-indoxyl-nonanoate; 5-bromo-4-chloro-3-indoxyl-nonanoate; 6-chloro-3-indoxyl-nonanoate; 6-bromo-3-indoxyl-nonanoate; 5-bromo-3-indoxyl-nonanoate; alizarin-nonanoate; nitrophenyl-nonanoate; 4-methylumbelliferyl-nonanoate; naphthyl-nonanoate; aminophenyl-nonanoate; dichloroaminophenyl-nonanoate; 5-bromo-6-chloro-3-indoxyl-phosphate; dihydroxyflavone-phosphate; 3,4-cyclohexenoesculetin-phosphate; 5-bromo-4-chloro-3-indoxyl-phosphate; 6-chloro-3-indoxyl-phosphate; 6-bromo-3-indoxyl-phosphate; 5-bromo-3-indoxyl-phosphate; 6-fluoro-3-indoxyl-phosphate; alizarin-phosphate; nitrophenyl-phosphate; 4-methylumbelliferyl-phosphate; naphtholbenzein-phosphate; indoxyl-N-methyl-phosphate; 5-bromo-4-chloro-3-indoxyl-N-methyl-phosphate; naphthyl-phosphate; aminophenyl-phosphate; dichloroaminophenyl-phosphate. Without being limiting, a concentration of between 25 and 1000 mg/l is particularly suitable for the present invention.

Preferably, the esterase substrate is chosen from butyrate esterase, lipase and phosphatase substrates, and in particular from: 5-bromo-6-chloro-3-indoxyl-octanoate; 5-bromo-4-chloro-3-indoxyl-butyrate; 5-bromo-3-indoxyl-nonanoate and 5-bromo-6-chloro-3-indoxyl-phosphate.

The term peptidase substrate is intended to mean in particular proline-aminopeptidase, alanine-aminopeptidase, leucine-aminopeptidase, pyrrolidonyl-arylamidase, phenylalanine-aminopeptidase, Ala-Phe-Pro-peptidase and tyrosine-aminopeptidase substrates. These substrates are in particular compounds which combine the amino acid, or the corresponding peptide, and a p-nitroaniline, 7-aminomethylcoumarin, 7-aminophenoxazinone, naphthylamine, aminophenyl or dichloroaminophenyl radical, via a peptide bond. Mention may in particular be made of prolyl-p-nitroanilide, prolyl-7-amido-4-methylcoumarin, prolyl-dichloroamidophenol, alanyl-dichloroamidophenol, leucyl-p-nitroanilide, pyrroldonyl-7-amido-4-methylcoumarin, phenylalanyl-p-nitroanilide, Ala-Phe-Pro-7-amido-1-pentyl-phenoxazin-3-one and tyrosyl-dichloroamidophenol. Without being limiting, a concentration of between 25 and 1000 mg/l is particularly suitable for the present invention.

Preferably, the peptidase substrate is chosen from proline-aminopeptidase (or prolyl-arylamidase), leucine-aminopeptidase (or leucyl-arylamidase) and pyrrolidonyl-arylamidase substrates, and in particular from prolyl-p-nitroanilide, prolyl-7-amido-4-methylcoumarin, leucyl-p-nitroanilide and pyrrolidonyl-7-amido-4-methylcoumarin.

The term biological sample is intended to mean a clinical sample, derived from a specimen of biological fluid, or a food sample, derived from any type of food. This sample may thus be liquid or solid, and mention may be made, in a nonlimiting manner, of a clinical blood, plasma, urine or feces sample, nose, throat, skin, wound or cerebrospinal fluid specimens, a food sample from water, from drinks such as milk or a fruit juice, from yogurt, from meat, from eggs, from vegetables, from mayonnaise, from cheese; from fish, etc., a food sample derived from an animal feed, such as, in particular, a sample derived from animal meals.

In this respect, the invention relates to a method for detecting and/or identifying *Clostridium difficile*, characterized in that it comprises the following steps:
  a) providing a reaction medium comprising at least one beta-glucosidase substrate capable of identifying *C. difficile*,
  b) inoculating the medium with a biological sample to be tested,
  c) allowing for incubation, and
  d) detecting the hydrolysis of the beta-glucosidase substrate, indicative of the presence of *Clostridium difficile*.

According to one preferred embodiment of the invention, during step c), the incubation is carried out under anaerobic conditions.

According to one preferred embodiment of the invention, said beta-glucosidase substrate is chosen from alizarin-β-glucoside, magenta-β-glucoside (5-bromo-6-chloro-3-indoxyl-β-glucoside) and CHE-β-glucoside (3,4-cyclohexenoesculetin-β-glucoside).

Preferably, said beta-glucosidase substrate is at a concentration of between 25 and 1000 mg/l, more preferably between 50 and 400 mg/l.

According to one preferred embodiment of the invention, said reaction medium also comprises esculin. Preferably, the esculin is at a concentration of between 5 and 500 mg/l, preferably between 10 and 100 mg/l.

According to one preferred embodiment of the invention, said reaction medium also comprises at least one β-glucosidase inducer, preferably chosen from cellobiose or methyl-β-glucoside.

According to one preferred embodiment of the invention, said reaction medium also comprises at least one growth activator for *C. difficile* strains, preferably chosen from blood, serum and a reducing agent such as, in particular, cysteine, pyruvate or ferrous sulfide.

According to one preferred embodiment of the invention, said reaction medium also comprises at least one *C. difficile* spore germination inducer, preferably sodium taurocholate.

According to one preferred embodiment of the invention, said reaction medium also comprises at least one selective agent, preferably chosen from an antibiotic, such as, in particular, D-cycloserine, cefoxitin or cefotaxime, and an antifungal, such as, in particular, amphotericin B, fluconazole, itraconazole or voriconazole.

According to one preferred embodiment of the invention, said reaction medium also comprises at least a second enzyme substrate, preferably chosen from an osidase substrate, an esterase substrate and a peptidase substrate.

According to one preferred embodiment of the invention, said reaction medium also comprises at least one reducing agent, preferably cysteine.

The invention also relates to a reaction medium for the detection and/or the identification of *Clostridium difficile*, that comprises at least one beta-glucosidase substrate capable of identifying *C. difficile*.

According to one preferred embodiment of the invention, said beta-glucosidase substrate is chosen from alizarin-β-glucoside, magenta-β-glucoside (5-bromo-G-chloro-3-indoxyl-β-glucoside) and CHE-β-glucoside (3,4-cyclohexenoesculetin-β-glucoside).

Preferably, said beta-glucosidase substrate is at a concentration of between 25 and 1000 mg/l, and more preferably between 50 and 400 mg/l.

According to one preferred embodiment of the invention, said reaction medium also comprises esculin.

Preferably, the esculin is at a concentration of between 5 and 500 mg/l, preferably between 10 and 100 mg/l.

According to one preferred embodiment of the invention, said reaction medium also comprises at least one β-glucosidase inducer, preferably chosen from cellobiose or methyl-β-glucoside.

According to one preferred embodiment of the invention, said reaction medium also comprises at least one growth activator for *C. difficile* strains, preferably chosen from blood, serum and a reducing agent such as, in particular, cysteine, pyruvate and ferrous sulfide.

According to one preferred embodiment of the invention, said reaction medium also comprises at least one *C. difficile* spore germination inducer, preferably sodium taurocholate.

According to one preferred embodiment of the invention, said reaction medium also comprises at least one selective agent. Preferably, the selective agent is chosen from an antibiotic, preferably D-cycloserine, cefoxitin or cefotaxime, and an antifungal, preferably amphotericin B, fluconazole, itraconazole or voriconazole.

According to one preferred embodiment of the invention, said reaction medium also comprises at least a second enzyme substrate. Preferably, said second substrate is an osidase substrate, an esterase substrate or a peptidase substrate.

According to one preferred embodiment of the invention, said reaction medium also comprises at least one reducing agent, preferably cysteine.

The invention also relates to the use of a medium as defined above, for the detection and/or identification of *Clostridium difficile*.

The examples below are given by way of explanation and are in no way limiting in nature. They will make it possible to understand the invention more clearly.

EXAMPLE 1

Identification of Beta-Glucosidase Substrates Capable of Identifying *C. difficile*

On the basis of the present invention, the β-glucosidase substrates capable of detecting *Clostridium difficile* strains can be identified by those skilled in the art by means of the example below.

The potential β-glucosidase substrate is tested by incorporating it into a medium which allows the growth of *Clostridium difficile*, such as a selective medium, containing, for example, inhibitors for slowing down the growth of certain bacteria or of certain eukaryotes, or a nonselective medium, such as Columbia agar in a flask (ref 41244) or an egg base according to George et al. (see example 2).

Depending on the β-glucosidase substrate to be tested, it may be necessary to add an additional reagent, such as, in particular, an iron salt or an α-naphthol derivative, in order to reveal the hydrolysis product.

Preferably, the substrate to be tested is tested at a concentration of between 25 and 1000 mg/l. The medium thus prepared is dispensed into a consumable item, for example a Petri dish or a tube. A collection of strains comprising at least one *C. difficile* strain is inoculated, preferably a single strain per medium. The medium is then incubated under anaerobic conditions at a suitable temperature, generally between 20 and 50° C., preferably between 30 and 40° C.

The suitable substrates are those for which hydrolysis by the *C. difficile* strain(s) is detected after incubation. The detection is carried out by observing a variation in the optical properties (colored or fluorescent colonies and/or medium) either visually under natural, artificial or UV light, or by means of a suitable instrument, in particular spectrophotometer, fluorimeter, luminometer or image analyzer.

EXAMPLE 2

Strains of the genus *Clostridium* spp were tested on 6 different media, each containing a chromogenic beta-glucosidase substrate. The dishes are then read at 48 h in order to determine the specificity of each substrate.

1. Medium and Microorganisms

The base of the media is an egg yolk base according to George et al., the composition of which is the following (in g/l):

| | |
|---|---|
| Proteose peptone No. 3 | 40 |
| Disodium hydrogen phosphate | 5 |
| Potassium dihydrogen phosphate | 1 |
| Sodium chloride | 2 |
| Magnesium sulphate | 0.1 |
| Agar | 20 |
| Sterilize at 116° C. and Cool to 50° C. | |
| 50% egg yolk in sterile saline | 5 ml |

This medium is separated into 6 fractions. One of the following substrates is added to each of these fractions: magenta-β-glucoside (80 mg/l), alizarin-β-glucoside (50 mg/l), CHE-β-glucoside (300 mg/l), 8-hydroxyquinoline-β-glucoside (300 mg/l), DHF-β-glucoside (300 mg/l), blue-β-glucoside (150 mg/l). The substrates were commercial substrates obtained from companies specializing in the supply of synthetic enzyme substrates. The alizarin-based substrate was synthesized according to the protocol described in patent application EP 1235928. The CHE-based substrate was synthesized according to the protocols described in patent application EP0900230.

2. Tests

The media are dispensed into Petri dishes.

The inoculation is carried out from precultures prepared for 48 h at 37° C. under anaerobic conditions.

A suspension of physiological saline at 0.5 McF is prepared and then 1 µl of each suspension is deposited on each dish.

Readings are carried out after incubation for 48 h.

3. Results

|  | Incubation | Magenta-β-glucoside (80 mg/l) | | Alizarin-β-glucoside (50 mg/l) | | CHE-β-glucoside (300 mg/l)[1] | | DHF-β-glucoside (300 mg/l)[2] | |
|---|---|---|---|---|---|---|---|---|---|
| strains | time | Gr | Co | Gr | Co | Gr | Co | Gr | Co |
| *Clostridium difficile* | 48 h | 18/28 | 16/18 | 22/28 | 18/22 | 21/28 | 20/21 | 28/28 | 20/28 |
| Other *Clostridium* | 48 h | 17/17 | 6/17 | 16/17 | 2/16 | 17/17 | 6/17 | 12/14 | 3/12 |

Gr = growth; Co = coloration
[1] = +500 mg/l of ammoniacal iron citrate
[2] = +50 mg of ammoniacal iron citrate 4. Interpretation All the substrates made it possible to reveal C Alizarin-β-glucoside, magenta-β-glucoside (5-bromo-6-chloro-3-indoxyl-β-glucoside) and, in particular, CHE-β-glucoside (3,4-cyclohexenoesculetin-β-glucoside) exhibited good sensitivity with respect to *Clostridium difficile*.

EXAMPLE 3

Strains of the genus *Clostridium* spp were tested on four different media, each containing a chromogenic beta-glucosidase substrate and 300 mg/l of ammoniacal iron citrate, according to a protocol similar to that described in example 2. The base of the media was a Colombia base, and the substrates tested were the following:
  Blue-β-glucoside (5-bromo-3-indoxyl-β-glucoside) at a concentration of 300 mg/l,
  8HQ-β-glucoside (8-hydroxyquinoline-β-glucoside) at a concentration of 150 mg/l,
  alizarin-β-glucoside (1,2-dihydroxyanthraquinone-β-glucoside) at a concentration of 50 mg/l,
  DHF-β-glucoside at a concentration of 300 mg/l.

The dishes were then read at 48 h in order to determine the specificity of each substrate.

The results are shown below:

1. Test

The inoculation is carried out from precultures prepared for 48 h at 37° C. under anaerobic conditions.

A suspension in physiological saline at 0.5 McF is prepared and then the strains are inoculated using a 10 µl calibrated loop.

The readings are carried out after incubation for 24 hours at 37° C.

2. Results

For Growth:

The values indicated correspond to the diameter of the colonies.

|  | Incubation | DHF-β-glucoside (300 mg/l) | | Alizarin-β-glucoside (50 mg/l) | | 8-Hydroxyquinoline-β-glucoside (150 mg/l) | | Blue-β-glucoside (300 mg/l) | |
|---|---|---|---|---|---|---|---|---|---|
| strains | time | Gr | Co | Gr | Co | Gr | Co | Gr | Co |
| *Clostridium difficile* | 48 h | 10/10 | 10/10 | 10/10 | 8/10 | 10/10 | 5/10 | 10/10 | 10/10* |

Gr = growth ; Co = coloration; *= diffusion of trie coloration
All the substrates made it possible to reveal *C difficile*.

EXAMPLE 4

1. Medium and Microorganisms

Five media, each containing 48.10 g/l of Columbia base, 2.5 g/l of sodium taurocholate, 200 mg/l of ammoniacal iron citrate, 100 mg/l of CHE-beta-glucoside, and also an inhibitor system normally used in the media for *Clostridium difficile*, based on D-cycloserine, and varying concentrations of esculin and glucose (see following table):

|  | medium 1 | medium 2 | medium 3 | medium 4 | medium 5 |
|---|---|---|---|---|---|
| Glucose g/l | 1 | 0 | 1 | 1 | 1 |
| Esculin mg/l | 0 | 37.5 | 25 | 37.5 | 50 |

For Coloration Strength:

1 corresponds to the presence of a clear coloration of weak strength, 1.5 corresponds to the presence of a coloration that is intermediate between colorations 1 and 2, 2 corresponds to the presence of a clear coloration of medium strength, 2.5 corresponds to the presence of a coloration that is intermediate between colorations 2 and 3, 3 corresponds to the presence of a strong coloration.

|  |  | Medium 1 | | Medium 2 | | Medium 3 | | Medium 4 | | Medium 5 | |
|---|---|---|---|---|---|---|---|---|---|---|---|
|  |  | G | I | G | I | G | I | G | I | G | I |
| C. difficile 042 | 24 h | 2.5 | 2 | 1 | 2.5 | 2 | 2.5 | 2 | 2.5* | 2 | 2.5* |
| C. difficile 308 | 24 h | 1.5 | 2 | 1 | 3 | 1.5 | 3 | 1.5 | 3* | 1.5 | 3* |
| C. difficile 169 | 24 h | 1.5 | 1 | 1.5 | 2 | 1.5 | 1.5 | 1.5 | 1.5* | 1.5 | 1.5* |
| C. difficile 187 | 24 h | 1.25 | 2 | 0.75 | 2 | 1.25 | 2.5 | 1.25 | 2.5* | 1.5 | 2.5* |

G = Growth, I = Coloration strength, *= diffusion of the coloration

4. Interpretation

According to medium 2, the absence of glucose leads to a decrease in the size of the colonies, and esculin, for its part, has a positive effect on the strength of the coloration.

In media 3, 4 and 5, the two compounds were mixed. A more or less sizeable diffusion of the coloration in the agar is noted for media 4 and 5.

Medium 3 therefore represents the best compromise between growth improvement and coloration strength.

EXAMPLE 5

1. Medium and Microorganisms 107 strains were tested on two prototype media for *C. difficile*, the compositions of which are the following (per liter):

|  | Medium 1 | Medium 2 |
|---|---|---|
| Columbia base | 48.10 g | 48.10 g |
| Glucose | 1.25 g | 1 g |
| Taurocholate | 2.5 g | 2.5 g |
| Ammoniacal iron citrate | 0.2 g | 0.2 g |
| Autoclaving of the base and addition of the additives | | |
| CHE-β-glucoside | 0.100 g | 0.100 g |
| Esculin | / | 0.025 g |

Selective system in the 2 media according to George et al., "Selective and differential medium for isolation of *Clostridium difficile*", Journal of Clinical Microbiology Vol. 9, p. 214-219, 1979.

2. Tests

The inoculation is carried out from precultures prepared for 48 h at 37° C. under anaerobic conditions.

A suspension in physiological saline at 0.5 McF is prepared and then the strains are inoculated using a 10 µl calibrated loop.

The readings are carried out after incubation for 24 and 48 hours at 37° C.

3. Results

|  | Total strains | Incubation time | % of strains producing a | |
|---|---|---|---|---|
|  |  |  | Medium 1 | Medium 2 |
| Clostridium difficile | 31 | 24 h | 90 | 90 |
|  |  | 48 h | 94 | 94 |
| Other Clostridium | 34 | 24 h | 3 | 3 |
|  |  | 48 h | 3 | 6 |
| Other strains (Gram+, Gram−) | 42 | 24 h | 5 | 9 |
|  |  | 48 h | 12 | 32 |
|  | 107 |  |  |  |

4. Interpretation

The CHE-β-glucoside substrate exhibits good sensitivity with respect to *Clostridium difficile* from 24 h onward. The selectivity of the medium is itself also very satisfactory, since, at 24 h, only 8 strains out of 76, other than *Clostridium difficile*, grow on medium 1. It makes it possible to increase the *Clostridium difficile* coloration strength and to render homogeneous strains which have a heterogeneous appearance on medium 1.

In conclusion, the CHE-β-glucoside substrate exhibits good specificity and good sensitivity with respect to *Clostridium difficile* since it makes it possible to reveal close to 90% of the strains with a minimum of false positives from 24 h onward.

EXAMPLE 6

Fecal samples from patients who might be infected with a strain of *Clostridium difficile* were tested on 4 different media.

1. Medium and Microorganisms

The first medium (A) corresponds to the medium of example 1, to which D-cycloserine (250 mg/l) and cefoxitin (16 mg/l) have been added. The second medium (B) corresponds to medium 1 of example 5. The 3rd (C) and 4th (D) media are based on the chromID *Salmonella* medium of bioMerieux, free of its enzyme substrates, supplemented with cysteine at 0.5 g/l, and the selective system of which has been replaced with that of medium 1 of example 5. Medium C also comprises CHE-glucoside at 100 mg/l, ammoniacal iron citrate at 200 mg/l, sodium taurocholate at 2.5 g/l and glucose at 1.25 g/l. Medium D also comprises CHE-glucoside at 300 mg/l, ammoniacal iron citrate at 500 mg/l, sodium taurocholate at 1 g/l and 3% horse serum.

2. Tests

The media are dispensed into Petri dishes.

The inoculation is carried out from homogenized fecal samples.

Readings are carried out after incubation for 48 h.

3. Results

| | Medium A | | Medium B | | Medium C | | Medium D | |
|---|---|---|---|---|---|---|---|---|
| | No.[1] | Color | No. | Color | No. | Color | No. | Color |
| *Clostridium difficile* | 13 | Black | 12 | Black or with a gray center | 14 | Gray | 14 | Black |
| Others | 2 | Black | 2 | Black | 10 | Colorless to white | 8 | Colorless to white |
| | 15 | Colorless to white | 7 | Colorless to white | | | | |

[1]No. = Number of microorganisms detected.

4. Interpretation

These four media enabled easy detection of the *Clostridium difficile* strains present in muitimicrobial samples such as feces. Surprisingly, the detection was even easier on media C and D, which are, however, based on a medium for bacteria with a facultative aerobic metabolism. However, the average size of the *C. difficile* colonies was greater on medium A (3.8 mm) than on media B, C and D (1.6, 2.1 and 2 mm, respectively). For media C and D, this lesser growth was compensated for by a better selectivity (total or partial inhibition of the other microorganisms) and a better specificity, black colonies not being produced by any strain not belonging to the species *C. difficile*.

The variation in the concentration of the beta-glucosidase substrate between media C and D leads to a modification of the coloration contrast without disturbing the effectiveness of the medium in terms of number of strains correctly detected.

The invention claimed is:

1. A method for detecting and/or identifying *Clostridium difficile*, comprising:

inoculating a culture medium with a biological sample to be tested, the culture medium allowing for the growth of *C. difficile* and comprising at least one beta-glucosidase substrate capable of identifying *C. difficile;* incubating the inoculated culture medium under anaerobic conditions; and detecting hydrolysis of the beta-glucosidase substrate when *C. difficile* is present in the biological sample.

2. The method of claim 1, wherein said beta-glucosidase substrate is selected from the group consisting of alizarin-β-glucoside, magenta-β-glucoside (5-bromo-6-chloro-3-indoxyl-β-glucoside) and CHE-β-glucoside (3,4-cyclohexenoesculetin-β-glucoside).

3. The method of claim 1, wherein said beta-glucosidase substrate is at a concentration of between 25 and 1000 mg/l.

4. The method of claim 1, wherein said culture medium further comprises esculin.

5. The method of claim 4, wherein the esculin is at a concentration of between 5 and 500 mg/l.

6. The method of claim 1, wherein said culture medium further comprises a β-glucosidase inducer.

7. The method of claim 1, wherein said culture medium further comprises at least one growth activator for *C. difficile* strains.

8. The method of claim 1, wherein said culture medium further comprises at least one *C. difficile* spore germination inducer.

9. The method of claim 1, wherein said culture medium further comprises at least one selective agent selected from the group consisting of an antibiotic and an antifungal.

10. The method of claim 1, wherein said culture medium further comprises at least a second enzyme substrate.

11. The method of claim 1, wherein said culture medium further comprises at least one reducing agent.

* * * * *